United States Patent [19]

Barone et al.

[11] Patent Number: 4,705,516
[45] Date of Patent: Nov. 10, 1987

[54] SETTING FOR A CARDIAC VALVE

[76] Inventors: Hector D. Barone; Jose R. Martin, both of Maza 1869/73, Buenos Aires, Argentina

[21] Appl. No.: 553,706

[22] Filed: Nov. 21, 1983

[30] Foreign Application Priority Data

Apr. 20, 1983 [AR] Argentina ............................ 292760

[51] Int. Cl.⁴ .............................................. A61F 2/24
[52] U.S. Cl. .................................................... 623/2
[58] Field of Search .............................. 3/1.5, 1; 623/2

[56] References Cited

U.S. PATENT DOCUMENTS 3,997,923  12/1976  Possis ...................................... 3/1.5
4,451,936   6/1984  Carpentier et al. ...................... 3/1.5

Primary Examiner—Ronald L. Frinks
Attorney, Agent, or Firm—Scully, Scott, Murphy & Presser

[57] ABSTRACT

A valve prosthesis for controlling the flow of blood through a cardiac opening in which a stent (b) is adapted to be permanently secured to the cardiac tissue around a cardiac opening (a) and the stent (b) forms a cylindrical opening having a preset inside diameter not less than the diameter of the cardiac opening (a) or is slightly larger than the diameter of the cardiac opening (a). A valve member (c) is releasably connected to stent (b) to control the flow of blood through the cardiac opening (a). The valve member (c) may be releasably connected to the stent (b) by means of a set of teeth (3) that are wedged into an inside circumferential groove (2) extending around the stent ring (b') or a thread set (3) can engage a thread (2) on the stent ring (b').

10 Claims, 7 Drawing Figures

SETTING FOR A CARDIAC VALVE

BACKGROUND OF THE INVENTION

This invention relates to a stent or supporting frame for cardiac valves which incorporates a positive improvement in cardiac prosthesis matter. This device permits its use in all the anatomic positions of the heart: mitral, aortic, tricuspid and pulmonar. More over, the device formed by the stent and the valve may be used in extra-anatomic positions, i.e. valvulate ducts and total cardiac prosthesis.

Noteworthy is the easy manner by means of which this invention solves the submitted problem. The coupling system of the prosthesis may be used when the stent is in supra or infra annular positions in relation to the anatomic positions of the heart, in such a manner that it permits the total usefulness of the implantation diameter, which shall be completely occupied by the prosthesis.

Thus the final result in which is referred to the effective area is perfectly similar to that obtained with conventional prosthesis. Another important advantage provided by this device is its universal application, that is to say, that the device can be adapted to many kind of valves, such as for example, dura mater valves, disk valves, ball cage valves, porcine valves, pericardium valves or many other ones.

Consequently, this invention permits one to take advantage of all the improvements of the valve to be used with this device, and adding to those advantages the very important property of significantly reducing the operation period during which blood is circulated outside the body, both at the initial transplantation, as well as at later times, taking into consideration the eventual prosthetic dysfunctions.

BRIEF DESCRIPTION OF THE DRAWINGS

For a better clarification and understanding of the object of this invention, same has been shown with different figures in which is represented the new stent in one of the preferred forms of the embodiment, all of same as an example, in the following manner.

Figure 1:
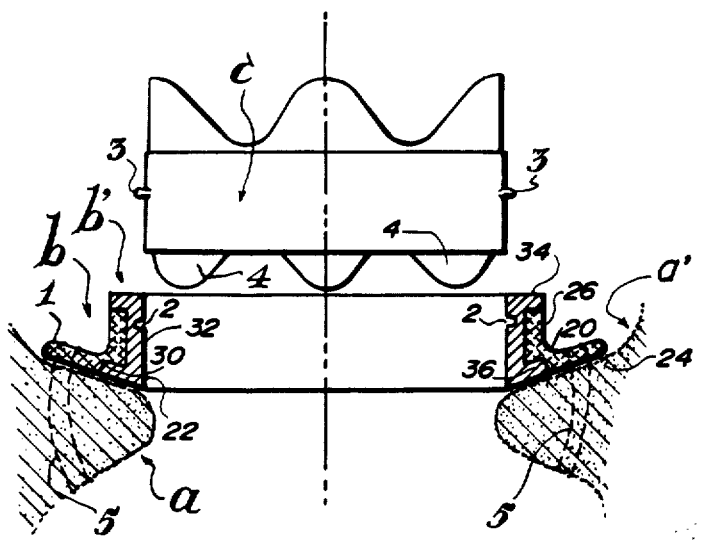
FIG. 1 is a diametrical section of the stent implanted in the blood passage of the ventricle toward the aorta.

It may be appreciated that because the diameter of ring B is larger than the diameter of the passage a, the ring that is fixed through suture, is spaced from the blood passage opening, it is clearly appreciated that the above mentioned ring that constitutes the stent has the tooth, thread bayonet insert, "sieger" ring, pressure or other mean to mesh the framework of the artificial cardiac valve that is also shown in FIG. 1.

Figure 2:
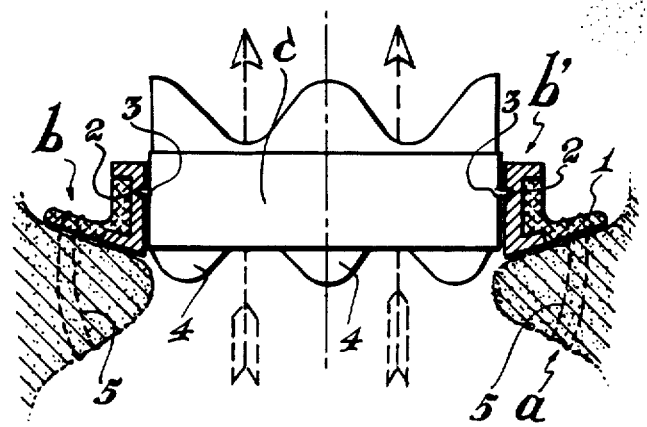

FIG. 2 is a diametrical section of the same assembly of the foregoing figure but with the valve connected to the stent to control the flow of blood from the ventricle to the aorta. The passage of blood through opening a is not hindered as much as the stent is spaced from the passage a.

Figure 3:
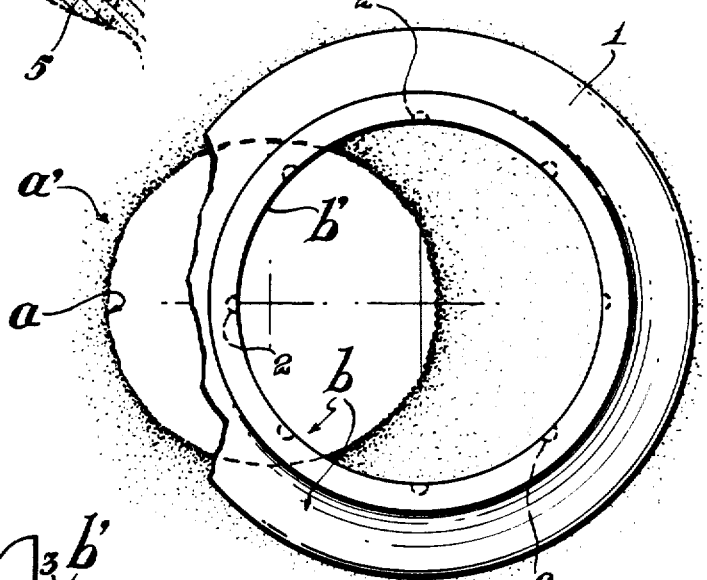
Figure 4:
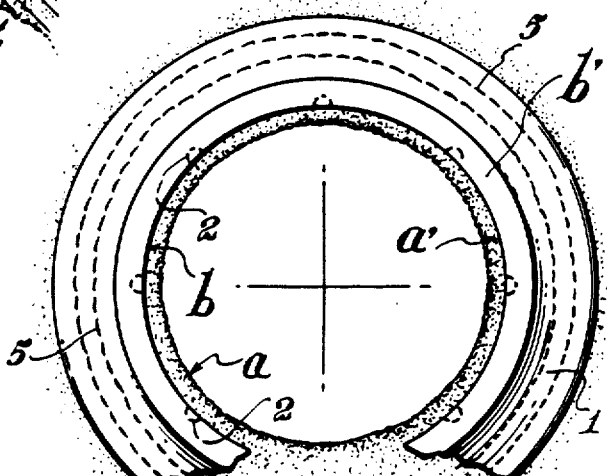

FIG. 3 is a plan view of the blood pressure orifice the diameter of which is smaller than the diameter of the valve-holder stent that it is also shown in the figure FIG. 4 is another a plan view of the blood passage orifice but with the stent shown concentrically placed around the blood passage. As the inside opening of this ring is larger than the diameter of the blood passage opening, a concentric edge is provided around the blood passage to compensate for the thickness of the blood flow control means (not shown in the figure).

Figure 5:
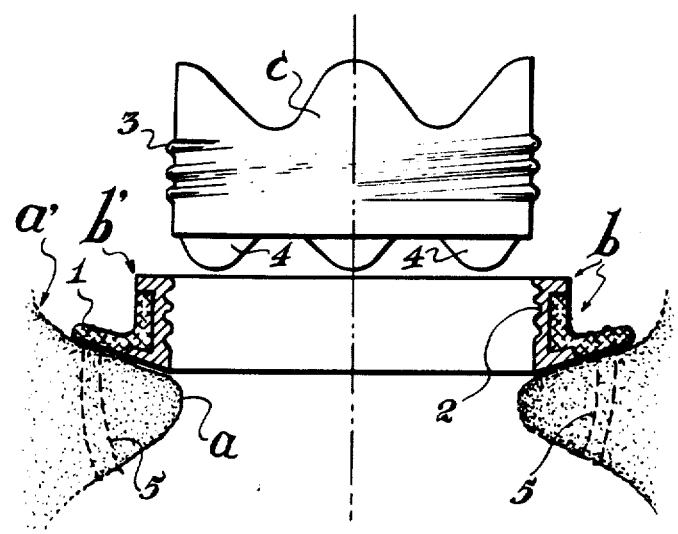

FIG. 5 is a sectional view similar to that of FIG. 1, but showing that the adaptation insert of the valve on the stent is threaded.

Figure 6:
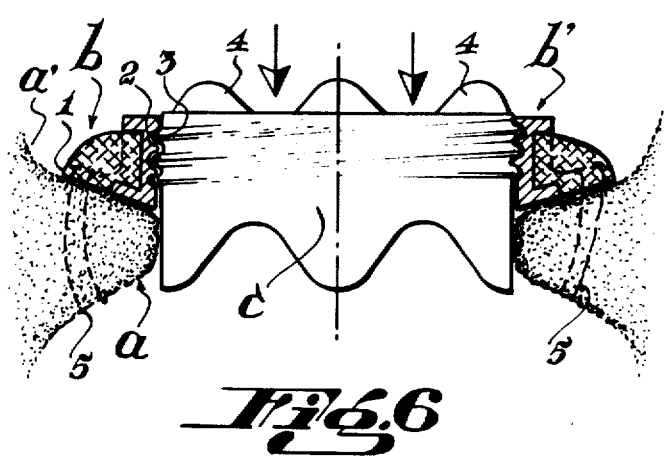

FIG. 6 shows a valve section secured to the stent, and placed in a supraannular mitral position.

Figure 7:
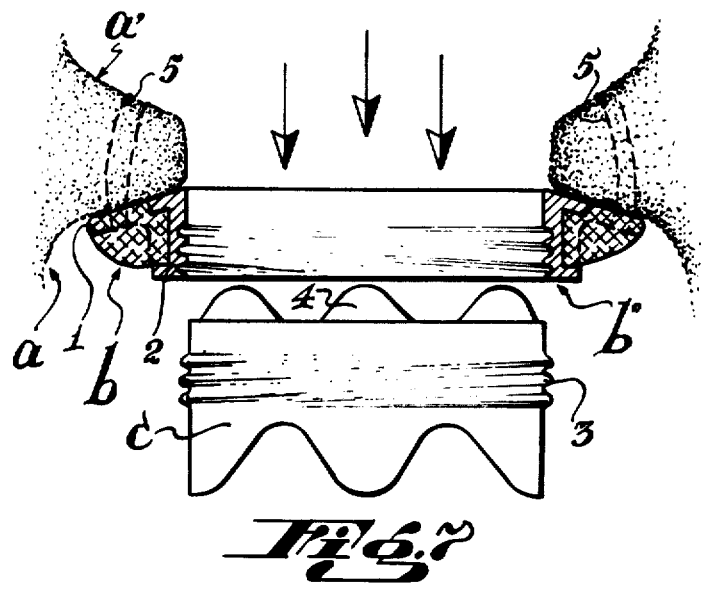

FIG. 7 is shows the stent in an infra-annular mitral position.

DETAILED DESCRIPTION OF THE PREFERRED EMBODIMENTS

In the different figures the same reference letters and numbers indicate the corresponding or identical parts or elements.

As is shown in the drawings, a is the blood passage opening from one cavity of the heart to the other which has been surgically operated. This opening a has an edge a' that is the place where the base face 1 of the stent b is supported the ring b' of stent b includes recess 2, which may be engaged by a wedge, a thread or other mean, to connect the cardiac valve c, which has a teeth or thread set 3 to stent b. This insert relation 2-3 may be of indistinct means provided that through wedge the valve c with its opening 4 be used for its specific function.

Ring b, which constitutes the permanent assembly stent of the prosthesis, has a diameter larger than the diameter of opening a, so that when the stent b is concentrically assembled, as is shown in FIGS. 1, 4, 5 and 6, there is a small edge sufficient to compensate the thickness of the wall of valve c.

In this centered position, stent b is fixed with its base 1 on edge a' through suture 5 in a permanent form so that, the stent b remains as support for valve c, that which is removable in case of dysfunction or other reason. Thus the re-exchange of valve c may be effected in the source of few minutes.

As the thickness of stent b, when concentrically implanted, remains spaced from the opening a, the stent does not limit the passage of blood from one cavity to the other, therefore, the blood flow is particularly the same as one what would be obtained using the same valve without the stent b.

As it was above stated, the stent b, centered marginally around the passage opening a, is of a permanent nature, so the valve c may be replaced in a rapid operation.

More specifically, stent b is adapted to be permanently secured to the cardiac tissue around cardiac opening a, and the stent forms a cylindrical opening having a preset inside diameter not less than the diameter of the cardiac opening. Valve member c is releasably connected to stent b to control the flow of blood through the cardiac opening a.

With reference to FIGS. 1-4, stent b may further form an inside circumferential groove 2 facing and in communication with the cylindrical opening formed by the stent. Valve member c includes a tubular sidewall, and a plurality of teeth 3 extending outward from this sidewall; and, in use, teeth 3 are wedged into circumferential groove 2 to connect the valve member b releasably to the stent. In use, blood flows through cardiac opening a in a first direction, as shown by the arrows in FIG. 2, and preferably teeth 3 of the valve member c and the circumferential groove 2 of the stent b are located completely outside the projection of the cardiac opening in that first direction.

Preferably, stent b includes outside collar member 20 and inside collar member 22; and, in turn, the outside collar member includes circumferential flange portion 24 and tubular portion 26, and the inside collar member includes bottom, circumferential flange portion 30, tubular portion 32 and top circumferential flange portion 34. Outside collar member 20 is adapted to be permanently secured to the cardiac tissue; and, in use, inside collar member 22 is connected to the outside collar member 20, and valve member c is releasably connected to the inside collar member.

More specifically, circumferential flange portion 24 of collar member 22 is adapted to be permanently secured to the cardiac tissue, and tubular portion 26 of the outside collar member is connected to flange portion 24 and extends outward therefrom. Bottom, circumferential flange portion 30 of the inside collar member 24 extends below tubular portion 26 of outside collar member 24, and, in use, flange portion 30 is captured between the cardiac tissue and the outside collar member 20 to connect inside collar member 24 to the outside collar member. In particular, tubular portion 26 of collar member 24 includes an inside circumferentially extending face, and a bottom recess 36 circumferentially extending around and radially extending outward from that inside face; and, as clearly shown in FIGS. 1 and 2, circumferential flange portion 30 of the inside collar member is captured in recess 36.

Tubular portion 32 of inside collar member 22 is connected to circumferential flange portion 30 and extends outward therefrom; and top flange 34 of collar member 22 extends outward from tubular portion 32, directly above tubular portion 26 of outside collar member 22 to further connect the inside collar member to the outside collar member.

MAIN OBJECT

As a main object, this invention comprises a stent for cardiac valves, which includes a holder ring b that is fixed through suture 5 to the cardiac tissues a' so as to provide a permanent base for a replaceable cardiac valvular prosthesis c, and is characterized in that the holder ring b, which constitutes the permanent stent has an internal diameter not less than the diameter of the blood passage a from one cavity to other; and more particularly in that, on the one hand, the above mentioned holder ring b, is concentric to the edges of the blood passage a, and is fixed through suture 5 to the cardiac tissues a' while on the other hand, said holder ring b is provided in its circumference marginally of the same opening of passage a, with a recess 2 receive the re-exchangeable assembly of valvular prosthesis c.

It is certain that in putting this invention into practice, amendments may be introduced to the construction and form of the above described stent without departing from the scope of this invention specified in the following claims.

Having described and illustrated the nature and the main object of this invention, as well as the form in which same may be put into practice, it is hereby claimed as exclusive property and rights:

1. A valve prosthesis for controlling the flow of blood through a cardiac opening having a diameter and formed by cardiac tissue, the valve prosthesis comprising:
   a stent adapted to be permanently secured to the cardiac tissue around the cardiac opening, and forming
   (i) a cylindrical opening having a preset inside diameter not less than the diameter of the cardiac opening, and
   (ii) an inside circumferential groove facing and in communication with the cylindrical opening; and
   a valve member releasably connected to the stent to control the flow of blood through the cylindrical opening and, thereby, through the cardiac opening, and including
   (i) a tubular sidewall, and
   (ii) a set of teeth extending outward from the sidewall, and wedged into the circumferential groove of the stent to connect the valve member releasably to the stent.

2. A valve prosthesis according to claim 1, wherein the inside diameter of the cylindrical opening is slightly larger than diameter of the cardiac opening to provide a small clearance between the stent and the cardiac opening.

3. A valve prosthesis according to claim 1, wherein blood flows through the cardiac opening in a first direction, and the teeth of the valve member and the groove of the stent are adapted to be located completely outside the projection of the cardiac opening in the first direction.

4. A valve prosthesis according to claim 1, wherein: the stent includes
   (i) an outside collar member adapted to be permanently secured to the cardiac tissue, and
   (ii) an inside collar member connected to the outside tubular member; and
   the valve member is releasbly connected to the inside collar member.

5. A valve prosthesis according to claim 4 wherein: the outside collar member includes
   (i) a circumferential flange portion adapted to be permanently secured to the cardiac tissue, and
   (ii) a tubular portion connected to the circumferential flange portion, and extending outward therefrom; and
   the inside collar member includes
   a bottom, circumferential flange portion extending below the tubular portion of the outside collar member, and adapted to be captured between the cardiac tissue and the outside collar member to connect the inside collar member to the outside collar member, and
   (ii) a tubular portion connected to the circumferential flange portion of the inside collar member, and extending outward therefrom.

6. A valve prosthesis according to claim 5, wherein: the tubular portion of the outside collar member includes
   (i) an inside circumferentially extending face, and
   (ii) a bottom recess circumferentially extending around and radially extending outward from the inside face; and
   the circumferential flange portion of the inside collar member is captured in said recess.

7. A valve prosthesis according to claim 6, wherein the inside collar member further includes a top circumferential flange extending outward from the tubular portion of the inside collar member, directly above the tubular portion of the outside collar member to further connect the inside collar member to the outside collar member.

8. A valve prosthesis according to claim 7, wherein:

the inside collar member forms an inside circumferential groove facing and in communication with the cylindrical opening;

the valve member includes a tubular shaped body, and a set of teeth extending outward from the tubular body; and the teeth of the valve member are wedged into the circumferential groove to connect the valve member releasably to the stent.

9. A valve prosthesis according to claim 1, wherein:

the valve member includes a tubular sidewall, and connecting means secured to the sidewall and connecting the valve member releasably to the stent; and the sidewall of the valve member is adapted to radially project outside the cardiac opening to guide blood flowing therethrough away from the connecting means.

10. A valve prosthesis according to claim 9, wherein blood flows through the cardiac opening in a first direction, and the sidewall of the valve member has a diameter not less than the diameter of the cardiac opening, and is adapted to be located completely outside the projection of the cardiac opening in the first direction.

* * * * *

UNITED STATES PATENT AND TRADEMARK OFFICE
CERTIFICATE OF CORRECTION

PATENT NO. : 4,705,516
DATED : November 10, 1987
INVENTOR(S) : Hector D. Barone, et al.

It is certified that error appears in the above-identified patent and that said Letters Patent is hereby corrected as shown below:

Column 2, line 23: "thread set 3" should read as --thread set 3,--

Column 2, line 35: "for valve c, that which" should read as --for valve c, which--

Column 2, line 38: "in the source" should read as --in the course--

Column 4, Claim 4, line 33: "valve member is releasbly" should read as --valve member is releasably--

Signed and Sealed this

Fourteenth Day of June, 1988

Attest:

DONALD J. QUIGG

*Attesting Officer*   *Commissioner of Patents and Trademarks*